United States Patent [19]

Gross et al.

[11] Patent Number: 5,253,649
[45] Date of Patent: Oct. 19, 1993

[54] PROCESS FOR THE MEASUREMENT OF BLOOD CIRCULATION BY MEANS OF NON-RADIOACTIVE MICROSPHERES

[75] Inventors: Rainer Gross, Wuppertal; Wolfgang Paffhausen, Leverkusen; Andreas Schade, Essen; Gerd Heusch, Neuss, all of Fed. Rep. of Germany

[73] Assignee: Triton Technology, Inc., San Diego, Calif.

[21] Appl. No.: 712,004

[22] Filed: Jun. 7, 1991

[30] Foreign Application Priority Data

Jun. 14, 1990 [DE] Fed. Rep. of Germany ....... 4019025

[51] Int. Cl.$^5$ ............................................. A61B 5/026
[52] U.S. Cl. ..................................... 128/691; 424/489; 436/56
[58] Field of Search ........................ 128/691, 692, 666; 356/39, 40, 317, 318; 424/9, 423, 486, 489, 497; 436/56; 250/461.2, 341

[56]  References Cited

U.S. PATENT DOCUMENTS

| 3,677,648 | 7/1972 | Dorsch | 356/40 |
| 4,115,699 | 9/1978 | Mizuta et al. | 250/461.2 |
| 4,295,199 | 10/1981 | Curry et al. | 250/461.2 |
| 4,499,052 | 2/1985 | Fulwyler | 250/461.2 |
| 4,616,658 | 10/1986 | Shell et al. | 128/691 |
| 4,709,703 | 12/1987 | Lazarow et al. | 128/654 |
| 4,745,285 | 5/1988 | Recktenwald et al. | 250/461.2 |
| 4,751,188 | 6/1988 | Valet | 250/461.2 |
| 4,811,741 | 3/1989 | Shell et al. | 128/691 |
| 4,874,949 | 10/1989 | Harris et al. | 356/40 |

Primary Examiner—Lee S. Cohen
Assistant Examiner—K. M. Pfaffle
Attorney, Agent, or Firm—William C. Fuess

[57] ABSTRACT

An improved process for the measurement of blood circulation by means of colored microspheres is presented, which process replaces the previous counting procedure when using colored microspheres by a rapidly reproducible measurement method. This avoids the complicated and expensive use of radioactively labelled microspheres. At the same time, a coloring process for the preparation of the microspheres is presented which is distinguished by homogeneous and intensive coloration of the microspheres.

13 Claims, 2 Drawing Sheets

PROCESS FOR THE MEASUREMENT OF BLOOD CIRCULATION BY MEANS OF NON-RADIOACTIVE MICROSPHERES

REFERENCE TO RELATED APPLICATIONS

The present application is related to U.S. patent application Ser. No. 07/656,230 for COLORED MICROSPHERES HAVING A KNOWN PHOTOMETRIC SPECTRUM FOR MEASURING AND TRACING FLUID MIXING AND FLOW, PARTICULARLY BLOOD FLOW TO TISSUE filed Feb. 14, 1991; which related application is to inventors including the same Gerd Heusch who is an inventor of the invention contained within the present application.

BACKGROUND OF THE INVENTION

1. Field of the Invention

The invention relates to a process for the measurement of the blood circulation of organ and tissue specimens by carrying out the following process steps:
1. Coloration of small plastic spheres
2. Introduction of the plastic spheres into the blood circulation
3. Sampling of a plurality of tissue and/or blood specimens
4. Determination of the number of plastic spheres in the specimens sampled
5. Determination of blood circulation using the values obtained by step 4.

Furthermore, the invention relates to a colouring process for the coloration of the microspheres used in the abovementioned process.

2. Description of the Prior Art

The known principle of measuring blood circulation is based on the injection of labelled plastic spheres (hereinafter also called microspheres) into the bloodstream of a laboratory animal, subsequent sampling of blood or tissue specimens and determination of the number of microspheres in the individual specimens. Blood circulation of the specimens tested at the time of injection of the microspheres can then be determined from the concentration of the microspheres in the tissue and blood specimens and the injected amount of microspheres.

Implementation of this process using radioactively labelled microspheres is known. Labelling takes place by incorporating various radioactive isotopes into the material comprising the spheres. Although this variant of labelling has been established as a standard method, it has nevertheless some serious disadvantages. The use of radioactive labels forces the user in particular to observe the various radiation protection laws. Thus, the laboratories in which measurements of blood circulation are carried out in this manner must be equipped accordingly and contamination of the persons involved in the tests must be avoided. Likewise, the laboratory animals must be housed in suitably controlled stables. This requires extensive structural measures and thus restricts the number of laboratories in which this process can be carried out. A further factor which makes the known process more expensive is that the animal carcasses contaminated in the course of this process must be stored in decay units before they can ultimately be disposed of. The isotopes usual for labelling are also expensive and rare, and their half lives, some of which are short, limit the use of the process in some cases. The apparatuses for measuring radioactivity (gamma counters, and the like) are also relatively complicated and expensive. In addition, the radioactively labelled microspheres have a density (1.3 g/ml) which differs from the density of the blood, resulting in unphysiological distribution of the microspheres in the bloodstream.

A process in which the radioactively labelled microspheres are replaced by those coloured with a colorant is described by European Patent Application EP 0,194,517 A1. In the process described, the microspheres are coloured in a solution comprising the salt of fat-soluble dyes and chloroform. Evaluation takes place by visual counting, in which the microspheres are counted either directly in the specimen or after being separated from the specimen and introduced into a special counter, a haemacytometer. This visual analytical process makes the method extremely work-intensive and prone to errors and prevents automation of the analysis. In addition, the process has further disadvantages. Thus the diameter of individual spheres from a specimen having a certain nominal diameter deviates by up to 50% from this nominal diameter. An error of this magnitude has an adverse effect on the precision of the entire measurement.

The object was therefore to improve the process for the measurement of blood circulation with the use of coloured microspheres such that measurement can be carried out rapidly, accurately and without large expenditure, in particular without employing large numbers of personnel. The object was in particular to improve the process for determining the number of microspheres in the tissue specimens.

SUMMARY OF THE INVENTION

The invention as characterised by the patent claims achieves the object by carrying out the following process steps:
A) Use of monodisperse microspheres
B) Homogeneous coloration of the microspheres
C) Isolation of the microspheres present in the individual specimens by dissolving the tissue or blood portions of the specimen, which leaves the microspheres and their dye content almost unchanged, followed by separating off the liquid phase
D) Determination of the number of microspheres in the specimen by eluting the dye and subsequent determination of the amount of dye eluted.

The new process has the advantage that the number of microspheres in the individual tissue specimens no longer has to be determined visually but is instead determined by an analytical process. The amount of dye eluted is determined by chromatographic or spectrophotometric processes known per se, such as gel chromatography or absorption spectroscopy.

The preferred spectroscopic method is absorption spectroscopy, which can be carried out rapidly and conveniently without any complicated analytical apparatus. When the absorption behaviour of a dye is known, the amount of dye of a specimen to be determined can be determined simply by measuring the absorption spectrum. Using conventional absorption spectrometers, absorption measurements can be carried out in a matter of seconds or less, so that a large number of measurements can be carried out within a relatively short time. The new process has the further advantage compared with the known one that the entire amount of dye of all microspheres present in a specimen is used for the measurement, while in the case of visual counting of a specimen only a representative sample can be measured for practical reasons, due to the large number of microspheres within this specimen (several thousand). This limitation further impairs the precision of the conventional process.

Furthermore, it has been found that the implementation of the new process is significantly improved by using monodisperse and homogeneously coloured microspheres. A monodisperse specimen of microspheres in the context of the invention is present when the diameter of the individual spheres deviates from the nominal diameter of the specimen by less than 10%. A homogeneous and intensive coloration of the microspheres in the context of the invention is present when two arbitrarily representative samples of about 1,000 spheres from the total amount of coloured spheres (about $10^8$) differ by at most 3% in their dye content, i.e. in the absorption of the amount of dye eluted therefrom. The coloration of the microspheres has sufficient intensity when the amount of dye of about 1,000 spheres produces an extinction of $\geq 0.1$.

The detection limit is an extinction of about 0.005.

A preferred embodiment of the new process is characterised in that various charges of microspheres are coloured with spectrally distinguishable dyes and these differently coloured microspheres are injected into different areas of the blood vessels or into the bloodstream at different times.

Since in measurements of blood circulation it is desired to investigate, for example, the blood circulation through a tissue before, during and after elimination of damage produced or the effect of physiological or pharmacological influences on the blood circulation, the use of differently coloured microspheres is particularly advantageous. The use of different colours for injection at different times and/or at different injection sites makes it possible to obtain a time- and site-differentiated picture of the blood circulation through a tissue. The use of differently coloured microspheres is known from the process described in EP 0,194,517 Al, but is clearly aggravated by the disadvantageous visual counting procedure described above, in particular when the differently coloured spheres within a specimen are present in markedly different concentrations. However, the concentration of the individual dyes can be determined from the absorption spectrum of the solution in which different dyes are present, provided that the individual spectra of the particular dyes are known, by processes known per se, such as, for example, a matrix inversion technique (Computer Programs in Biomedicine 9, 1979, 19-38). However the prerequisite is that the absorption maxima of the individual dyes do not completely overlap. Furthermore, the colour strength during the residence time in the blood or in the tissue and during the dissolution of blood or tissue must be almost maintained, i.e. the colour strength of the microspheres isolated may differ from that of the originally coloured microspheres by at most 3%.

A further preferred embodiment of the new process is characterised in that monodisperse microspheres having a nominal diameter in the range between 7 $\mu$m to 30 $\mu$m, preferably between 10 $\mu$m to 15 $\mu$m, and a tolerance of at most 10% are used.

Microspheres of the preferred size can be used particularly advantageously in the measurement of blood circulation. The nominal diameter of a charge of microspheres is the average diameter of the microspheres of this charge selected from the range given in accordance with the desired measurement. In a monodisperse charge of microspheres, the diameters of individual spheres of this charge deviate from the nominal diameter by at most 10%. The use of polydisperse microspheres leads to blocking of vessels of very different sizes and, in the case of excessively low diameters, to recirculation phenomena and thus to large scattering and measurement errors.

A further preferred embodiment of the new process is characterised in that coloured microspheres are used having a specific density which is close to the density of blood, preferably between 1.00 g/ml and 1.10 g/ml, particularly preferably between 1.04 g/ml and 1.06 g/ml.

The use of spheres whose specific density differs only a little from the density of the constituents of the blood are better capable of following the bloodstream than spheres of the same dimension whose specific weight is significantly higher. Accordingly, substances whose density is in the range given are preferred when selecting the material from which the microspheres are prepared. Polystyrene proves particularly suitable.

A dyeing process for polystyrene microspheres for use in the new process for the measurement of blood circulation is characterised in that dyestuffs without any salt-forming groups, in particular disperse dyestuffs, are used for the dyeing.

Surprisingly, it has been found that the microspheres can also be dyed with conventional disperse dyestuffs, thus making the use of salt-forming, fat-soluble and water-insoluble dyestuffs, which are used exclusively in the process known from EP 0,194,517 Al, unnecessary. The use of the new dyestuffs even produces a more intensive and more homogeneous coloration of the microspheres. Disperse dyestuffs based on azo compound, anthraquinone compound and in particular fluorescent dyestuffs based on coumarin gave particularly good results.

BRIEF DESCRIPTION OF THE DRAWINGS

Below the new process is illustrated by way of example with reference to the drawing, in which.

DESCRIPTION OF THE PREFERRED EMBODIMENTS

Figure 1:
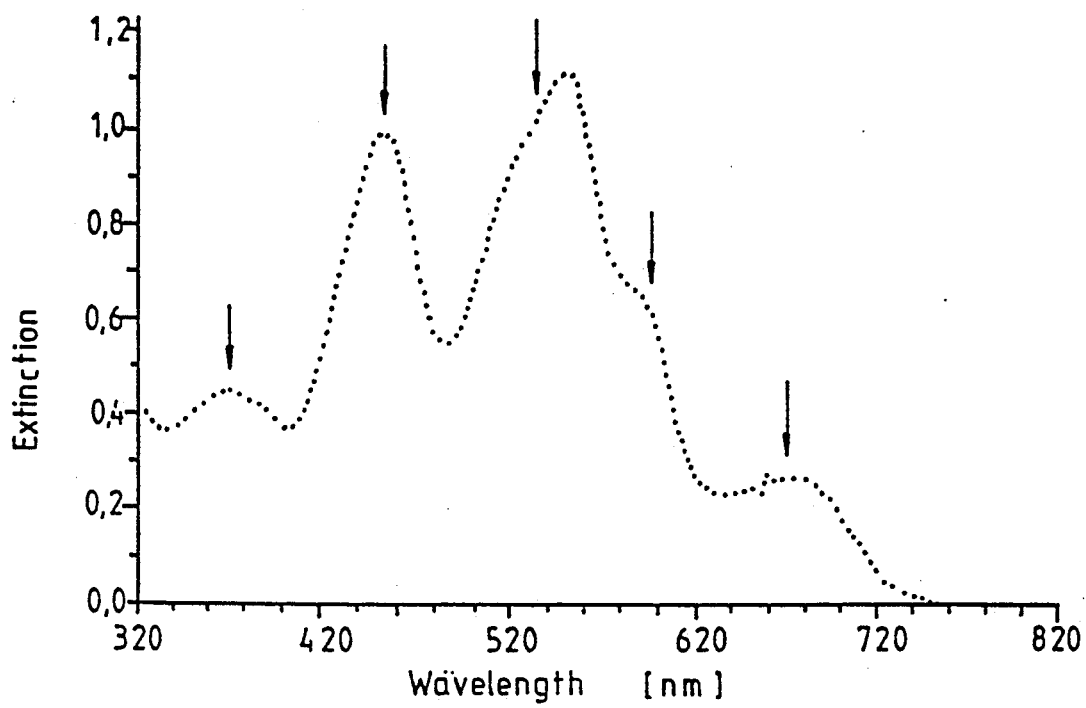
FIG. 1 shows a composite spectrum of a specimen in which 5 dyes are present.

For carrying out the process by way of example, polystyrene microspheres having a diameter of 10 $\mu$m and 15 $\mu$m and a variation coefficient of at most 5% in each case were used.

After purification with 70% strength ethanol, followed by drying, these microspheres were coloured in each case with one of the following dyestuffs:

1. UV absorber

-continued

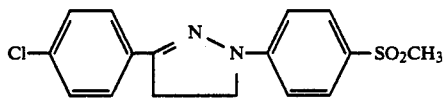

2. yellow

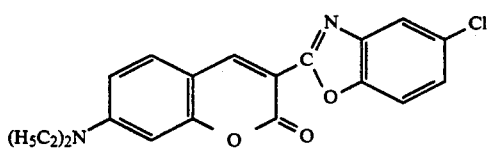

3. red-violet

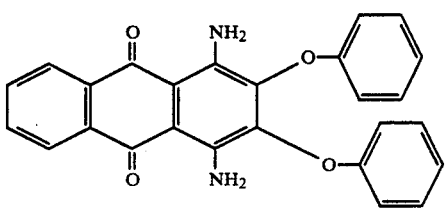

4. blue

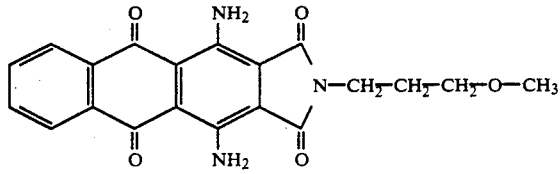

5. red

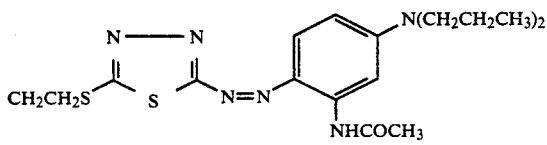

In order to colour the microspheres with the red and violet dyestuff, they were added to a solution consisting of 400 mg of the corresponding dyestuff, 2 ml of distilled water, 1 ml of a 1% strength aqueous solution of 65% of dichlorotoluene, 20% of methyl O-cresotinate and 15% of emulsifier composed of 55% of castor oil and 45% of the methanolamine salt of Marlon AS3 acid.

In order to dye the microspheres with the UV absorber, they were added to 10 ml of a mixture of 85% by volume of toluene and 15% by volume of dimethylformamide which had previously been impregnated with the dyestuff at 80° C.

The blue and the yellow dyestuff were first prepurified by recrystallisation in dichloromethane. The microspheres were then added to a mixture of 100 mg of purified dyestuff and 1 ml of 1,2,4-trichlorobenzene.

All mixtures composed of microspheres and dyestuffs were heated in boiling water (5 minutes in the case of the yellow and blue mixture, 90 minutes in the case of the UV absorber, red and violet mixture). The coloured microspheres were then prepurified by filtration, and the dye residues were then purified by resuspension in anhydrous ethanol, and ultrasound treatment and subsequent centrifuging while discarding the supernatant. After drying and resuspension in water, the spheres were divided into portions for later use in the experiment.

In order to measure the distribution of the blood flow in the circulation experiment, the coloured microspheres were again washed with ethanol and dried in vacuo. They were again washed with ethanol and dried in vacuo. They were then resuspended in physiological saline solution and added to the bloodstream by known methods, especially after suitable mixing, in the flowing blood into an organ artery or into the left atrium or left ventricle. By administering differently coloured microspheres, it was thus possible to record blood circulation states at different times.

After the experiment was completed, tissue and blood specimens were obtained in the usual manner and portioned.

The tissue specimens were portioned to weights between 0.3 to 2 g. The specimens were dissolved in 4-molar potassium hydroxide solution containing 2% of Tween 80 in a glass tube at 72° C. The solution was then filtered off with suction through microfilters. The remaining microspheres were washed together with the filters and dried.

To elute the dyestuff, the filters were transferred together with the microspheres into a test tube, and the dyestuffs were dissolved out by adding 100 $\mu$l of dimethylformamide. The dyestuff solution was then centrifuged at 2,000 g for 5 minutes and transferred into a small glass tube. This solution was freed from remaining particles by repeated centrifuging (3 minutes, 2,000 g).

Blood specimens were treated analogously.

Figure 2:
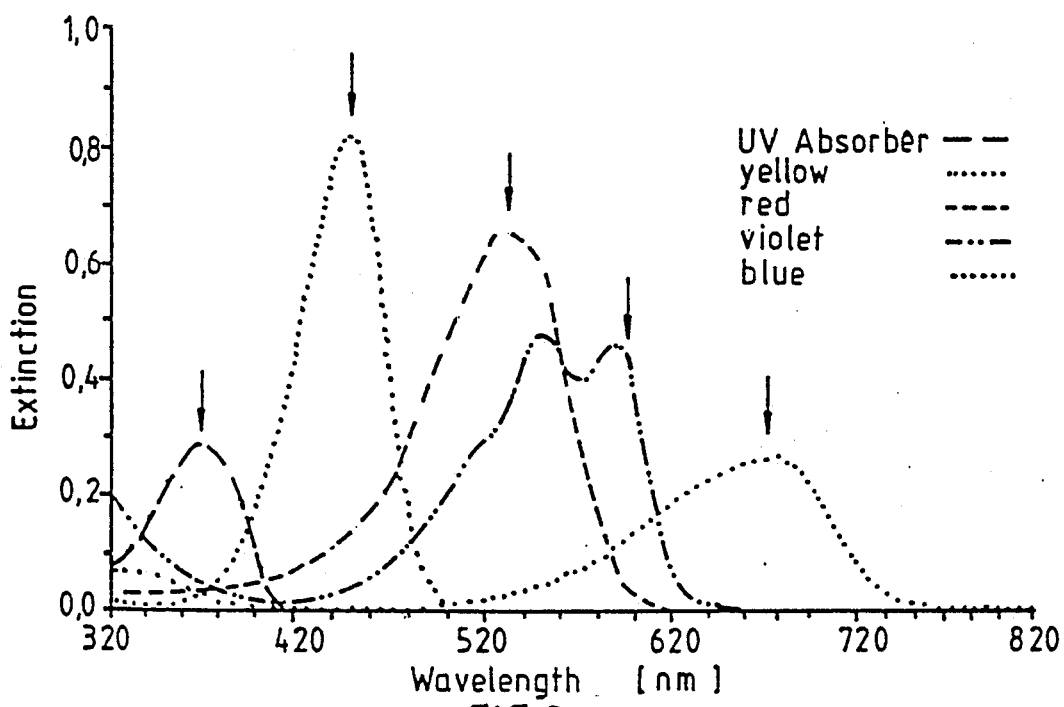
FIG. 2 shows the spectrum according to FIG. 1 divided into the individual spectra of the dyestuffs.

The absorption of the dyestuff solution obtained in this manner was measured using a diode array UV/VIS spectrophotometer having a spectral resolution of 2 nm in a wavelength range of 190 to 820 nm. FIG. 1 shows an extinction spectrum obtained in this manner of a specimen which contained 5 different dyestuffs. FIG. 2 shows the individual spectra of each of the dyestuffs which adds up to give the total spectrum. The dyestuffs were measured at wavelengths of 370 nm, 448 nm, 530 nm, 594 nm and 672 nm (indicated by arrows in FIGS. 1 and 2). By integrating 100 individual measurements of 0.1 sec duration each, the standard deviation of each individual absorption value was lowered to less than 0.1% of the average value.

Figure 3:
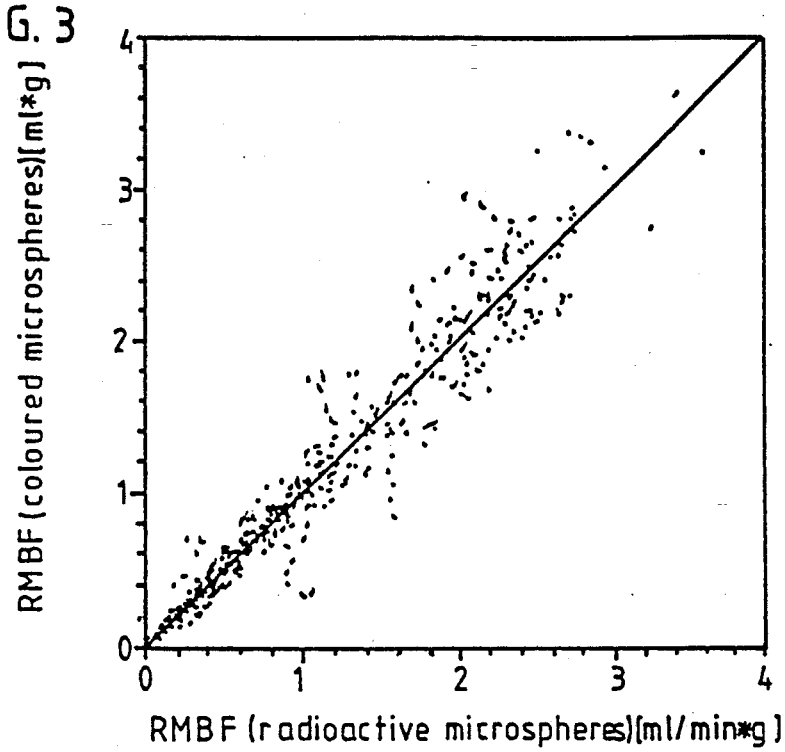
FIG. 3 shows a comparison of the new process (coloured microspheres) with the standard process (radioactive microspheres), carried out on 4 pigs with 1,080 data points.

In this manner, a very large number of specimens could be analysed. Thus, 1,080 and 1,813 specimens were compared for the comparative experiments shown in FIG. 3 and 4.

For comparison, one pair of each of coloured and radioactively labelled microsphere dispersions were injected into pigs and dogs under steady state conditions. In the first test series using pigs, injection took place directly into the left anterior coronary artery, and coronary circulation was increased at a constant coronary perfusion pressure by intracoronary adenosine infusion and regional myocardial ischaemia was caused by reducing the coronary perfusion pressure. In the second test series, radioactive and coloured microspheres were injected into dogs intraatrially. From the 1,080 specimens which were measured on pigs after intracoronary injection, a close correlation between the myocardia circulation measured with radioactively labelled microspheres and that measured with coloured microspheres was found, the correlation coefficient being 0.98. At y=1.00×X+0.01, the linear regression cannot be distinguished from the identity line (see FIG. 3).

Figure 4:
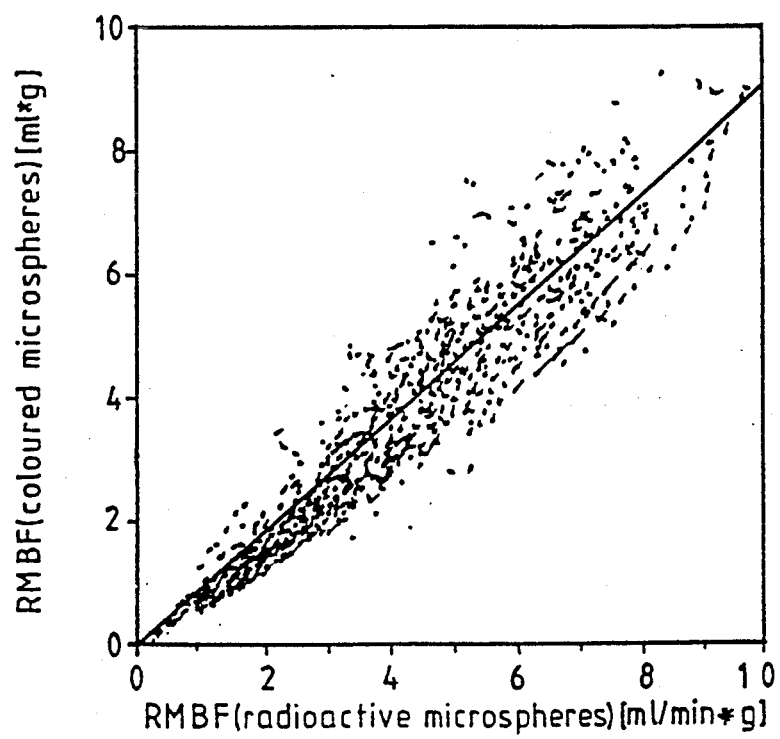
FIG. 4 shows a comparison of the new process (coloured microspheres) with a standard process (radioactive microspheres), carried out on 4 dogs with 1,813 data points.

During the systemic administration in the dog experiments, a total of 1,813 specimens were worked up. Here too a close correlation having a correlation coefficient of 0.97 was found, although the blood circulation determined by means of the radioactively labelled microspheres was systematically lower than that measured with coloured microspheres (FIG. 4). The straight line of regression is $y = 0.92 \times X - 0.19$. This deviation is probably a result of the large specific density of the radioactively labelled microspheres which strongly deviates from the density of the blood and the coloured microspheres.

What is claimed is:

1. In a process for the measurement of blood circulation within an organ tissue specimen of an animal including carrying out the process steps of:
   coloring microspheres with dye,
   introducing the microspheres into a blood circulation of the animal,
   sampling the organ tissue specimen of the animal, which specimen contains the microspheres,
   determining a number of microspheres in the specimen sampled, and
   calculating the blood circulation in the animal by use of the number of microspheres determined to be within the specimen,
wherein the improvement comprises the following steps:
   before the step of coloring, starting with a feedstock of uniform size, monodisperse, microspheres;
   wherein the step of coloring the microspheres serves to make the monodisperse microspheres homogeneous in coloration;
   wherein each microsphere has, as a consequence of being monodisperse in size and homogeneous in coloration with the other microspheres, an equal color intensity;
   after the sampling step, isolating the dye that is within the microspheres present in the specimen by
      dissolving tissue and blood portions of the specimen while leaving the microspheres with their dye content substantially unchanged, followed by
      eluting the dye from the microspheres; and
   wherein the step of determining the number of microspheres comprises:
      measuring the color intensity of the eluted dye; and
      calculating the number of microspheres that were within the specimen as the measured color intensity of the eluted dye divided by the color intensity per microsphere.

2. The process according to claim 1 wherein the color intensity of the eluted dye is determined by absorption spectroscopy.

3. The process according to claim 1 wherein different charges of microspheres are colored within the step of coloring using a plurality of spectrally distinguishable dyes and wherein these differently colored microspheres are injected during the step of introducing into different areas of vessels of the animal's bloodstream at different times.

4. The process according to claim 1 wherein the monodisperse microspheres have a nominal diameter in the range between 7 $\mu m$ and 30 $\mu m$.

5. The process according to claim 4 wherein the monodisperse microspheres used in the starting step have a nominal diameter from the range between 10 $\mu m$ and 15 $\mu m$.

6. The process according to claim 4 wherein monodisperse microspheres used in the starting step have a tolerance of at most 10% in their nominal diameter.

7. The process according to claim 1 wherein the microspheres used in the starting step have a specific density which is close to the density of blood.

8. The process according to claim 7 wherein microspheres used in the starting step have a specific density between 1.00 g/ml and 1.10 g/ml.

9. The process according to claim 8 wherein microspheres used in the starting step have a specific density between 1.04 g/ml and 1.06 g/ml.

10. The process according to claim 1 wherein the dye used for coloration in the coloring step is without salt-forming groups.

11. The process according to claim 10 wherein the dye consists essentially of compounds taken from the group consisting of azo compounds, anthraquinone compounds and coumarin compounds.

12. The process according to claim 11 wherein the dye consists essentially of fluorescent dyestuffs based on coumarin.

13. The process according to claim 10 wherein the dye without salt-forming groups consists essentially of disperse dyestuffs.

* * * * *